United States Patent [19]

Heinerman

[11] Patent Number: 4,511,752

[45] Date of Patent: Apr. 16, 1985

[54] PROCESS FOR THE HYDROISOMERIZATION OF PARAFFINS

[75] Inventor: Jacobus J. L. Heinerman, Amsterdam, Netherlands

[73] Assignee: Shell Oil Company, Houston, Tex.

[21] Appl. No.: 486,773

[22] Filed: Apr. 20, 1983

[30] Foreign Application Priority Data

Apr. 26, 1982 [NL] Netherlands .................. 8201716

[51] Int. Cl.$^3$ ............................................. C07C 5/13
[52] U.S. Cl. ..................................... 585/739; 585/747; 502/83
[58] Field of Search ................. 585/750, 739, 747; 502/83

[56] References Cited

U.S. PATENT DOCUMENTS

| | | | |
|---|---|---|---|
| 3,413,370 | 11/1968 | Fishel | 585/739 |
| 3,749,754 | 7/1973 | Eberly | 585/739 |
| 3,932,554 | 1/1976 | Takase et al. | 585/739 |
| 4,235,751 | 11/1980 | Del Pesco | 502/83 |
| 4,329,257 | 5/1982 | Sommer et al. | 502/83 |
| 4,417,090 | 11/1983 | Heinerman et al. | 585/739 |

FOREIGN PATENT DOCUMENTS

| | | | |
|---|---|---|---|
| 124189 | 5/1947 | Australia | 502/83 |
| 90442 | 10/1983 | European Pat. Off. | 585/739 |

Primary Examiner—Delbert E. Gantz
Assistant Examiner—Cynthia A. Prezlock
Attorney, Agent, or Firm—John M. Duncan

[57] ABSTRACT

A process is disclosed for the preparation of a more active paraffin hydrocarbon hydroisomerization catalyst from synthetic mica montmorillonite, preferably a nickel synthetic mica montmorillonite catalyst, which may also contain palladium, by treating the catalyst with one or more compounds comprising chlorine which can further release one or more protons and/or hydrogen chloride, and preferably by treating with hydrochloric acid.

8 Claims, No Drawings

PROCESS FOR THE HYDROISOMERIZATION OF PARAFFINS

BACKGROUND OF THE INVENTION

The invention relates to the use of metal silicate, particularly a synthetic mica montmorillonite (SMM), as catalyst in the catalytic conversion of hydrocarbons in the presence of hydrogen.

It is known to use metal silicates as catalysts for hydrocarbon conversions, such as cracking and isomerizing in the presence or absence of hydrogen. U.S. Pat. No. 4,022,684 describes an HF-treatment of a Pd-Ni SMM catalyst which reduces its isomerization activity.

It is known to use metal silicates as catalysts for hydrocarbon conversions, such as cracking and isomerizing in the presence or absence of hydrogen.

It is further known, that when subjected to a treatment with hydrogen fluoride the catalytic activity of certain metal silicates in hydroisomerization reactions is decreased.

It has now been found that the catalytic activity of the metal SMM silicates is dependent on the way in which they have been prepared; in particular it has been found that a treatment with one or more compounds comprising releasable active halogen other than fluorine, carried out during the preparation of certain metal silicates is highly effective. For instance, the reaction rate achieved in the catalytic hydroisomerization of unbranched paraffins is considerably higher when using certain metal silicates which have been treated with hydrochloric acid during their preparation than when using the same metal silicates which have not been treated with hydrochloric acid. This was found to be particularly so in the case of at least partly crystalline metal silicates having a crystal lattice substantially consisting of a triplex layer structure containing in the central layer octahedrally coordinated aluminum or at least part of the octahedrally coordinated aluminum replaced by one or more metals from Group VIII of the Periodic Table of Elements, and in the two outer layers tetrahedrally coordinated silicon or at least part of the tetrahedrally coordinated silicon replaced by aluminum.

SUMMARY OF THE INVENTION

The invention therefore relates to a process for the preparation of a catalytically active metal silicate wherein an at least partly crystalline metal silicate having a crystal lattice which consists substantially of a triplex layer structure containing in the central layer octahedrally coordinated aluminum, or at least part of the octahedrally coordinated aluminum replaced by one or more metals from Group VIII of the Periodic Table of Elements, and in the two outer layers tetrahedrally coordinated silicon, or substituting part of the tetrahedrally coordinated silicon by aluminum, is treated with one or more compounds comprising releasable active halogen other than fluorine.

DESCRIPTION OF PREFERRED EMBODIMENTS

In the process according to the invention these compounds, or their derivatives obtained after dissolving and/or heating them, react in such a manner with the metal silicates used as starting material that at least part of the halogen other than fluorine is incorporated as such in the catalytically active material thus obtained.

Preferably the metal silicate used as starting material in the process according to the invention is treated with a compound which comprises chlorine and which compound can further release, optionally after a heat treatment, one or more protons and/or hydrogen chloride. Especially suitable compounds comprise chlorine-containing acid and/or hydrocarbylammonium chloride and/or ammonium chloride; most preferably this compound contains hydrochloric acid.

Such layered metal silicates are known as smectites, which class of compounds includes, inter alia, montmorillonite. Especially suitable layered metal silicates for the process according to the invention consist at least partly of synthetic mica-montmorillonite (herein SMM) in which aluminum is partly substituted by nickel as the metal from Group VIII of the Periodic Table of Elements. Synthetic mica-montmorillonite is described by A. C. Wright et al in the J. of Catalysis 25 (1972), pp. 65-80.

If such nickel-substituted, synthetic mica-montmorillonite (abbreviated: Ni-SMM) is the starting material, the (eventual) catalytically active metal silicate contains preferably 20-36% nickel, and in particular 25-36% nickel, calculated on the overall composition.

Instead of nickel, other metals from Group VIII of the Periodic Table may be substituted for the octahedrally coordinated aluminum in the central layer of the crystal lattice as well. Cobalt in particular is eligible for the purpose.

The layered metal silicates used in the process according to the invention are preferably prepared via a hydrothermal synthesis route.

A metal silicate substantially consisting of Ni-SMM can suitably be prepared by entirely or largely substituting protons for the sodium ions of a water-dispersed sodium silicate by means of an ion exchanger in the H-form, and subsequently adding a nickel salt, an aluminum alcoholate, ammonia and, if desired, ammonium fluoride. The resulting slurry is partly evaporated and the gel obtained is subsequently heated to 250°-350° C. in an autoclave for several hours. The product obtained after filtration is dried at 70°-200° C. and if desired, calcined at 400°-600° C. for a fairly long time, for instance 30 minutes to 20 hours.

Ni-SMM can also suitably be prepared by adding nickel salt, an aluminum alcoholate and ammonium fluoride to silica dispersed in water, partly evaporating the resulting slurry, if desired, and subsequently introducing it into an autoclave for further treatment in the same manner as described in the former preparation method.

The Ni-SMM prepared by one of the above methods or an analogously prepared layered metal silicate containing a Group VIII metal other than nickel is then treated with hydrochloric acid according to the invention. Hydrochloric acid is an aqueous solution of hydrogen chloride and at a low temperature it may contain even more than 12 mol HCl/liter of water, which is more than about 40%w. Preferably from 0.4 to 40%w, and in particular from 15 to 25%w, of the hydrochloric acid to be used consists of hydrogen chloride. The treatment proper generally comprises contacting metal silicate and hydrochloric acid, in particular impregnating the metal silicate with the hydrochloric acid. The volume of the hydrochloric acid is advantageously chosen not larger than and in particular exactly equal to the pore volume of the metal silicate, so that the liquid can be completely absorbed.

After this treatment the metal silicate contains a percentage of chlorine which generally amounts to less than 20%w, based on the overall composition. The treatment may be extended by an additional drying step, for instance carried out at a temperature in the range between 70° and 200° C., over 15 to 90 minutes, in order to remove as much absorbed water as possible. The metal silicate is advantageously calcined after the treatment—and after a possible drying step. This calcination preferably comprises a heat treatment in air or in an inert gas at a temperature of from 400° to 600° C. for a period of from 30 minutes to 20 hours. The calcination allows part of the chlorine included earlier to escape. The quantity of initially included chlorine and the duration and temperature of the calcination are advantageously chosen such that after calcination the (eventual) catalytically active metal silicate preferably contains from 0.1 to 10, preferably from 0.2 to 2%w chlorine, calculated on the overall composition. A very suitable metal silicate as regards stability and activity will contain about 1%w chlorine.

In the process according to the invention the metal silicate is preferably loaded with one or more noble metals from Group VIII of the Periodic Table of Elements and/or compounds thereof, listed on the last page of the "Handbook of Chemistry and Physics", 55th Edition, CRC Press, Ohio, USA (1975). This "loading" is additional to the "substituting" that takes place in the crystal lattice of octahedrally coordinated aluminum. It is particularly preferred to load the metal silicate—notably before it is treated with a compound comprising realeasable active halogen other than fluorine—with 0.05-5, preferably 0.2-2%w of palladium, calculated on untreated metal silicate. To load the metal silicate with the noble metal any technique known in the art for the preparation of catalysts, such as impregnation, ion exchange or precipitation, may be used. In the present process preference is given to depositing the Group VIII noble metals on the metal silicate starting from an aqueous solution in which the metals occur in the cationic form. Especially preferred are ammonia solutions in which the Group VIII noble metals are present in the form of cationic complexes.

In a special embodiment a cross-linked, catalytically active metal silicate as described in the Applicant's Netherlands Patent Application No. 8201289 is used as starting material. In particular such a metal silicate is cross-linked before the treatment with a compound comprising releasable active halogen other than fluorine according to the invention is carried out. The metal silicate is preferably cross-linked by mixing with aluminum hydroxychloride and subsequently heating to at most 600° C.

Before the hydroisomerization of hydrocarbons is started, the catalyst is preferably activated by means of a hydrotreatment carried out at a temperature of from 150° to 600° C., in particular for at least several hours at a temperature of from 300° C. to 450° C. and at least atmospheric pressure.

It has been found that the first order reaction rate for the catalytic isomerization in the presence of hydrogen of paraffins with 4–7 carbon atoms is substantially higher (while maintaining a high selectivity—usually higher than 95%) when using a catalyst prepared according to the invention than when using a catalyst prepared without an aftertreatment with a halogen other than fluorine.

In the above-mentioned hydroisomerization according to the invention the starting material used is one or more paraffins, in particular paraffins with 4–7 carbon atoms, preferably mainly or entirely consisting of normal pentane or normal hexane or mixtures thereof. "Tops" obtained in the atmospheric distillation of mineral oil are very suitably used as starting material.

The result is that in the hydroisomerization according to the invention the greatest possible quantity of the paraffin present in the feed is converted into isomers of said paraffins having a higher degree of branching, whereas their degree of cracking into products with a lower number of carbon atoms than the molecules in the feed is kept to a minimum.

Suitable conditions for carrying out the hydroisomerization according to the invention are: a temperature between 150° and 330° C.; a space velocity between 0.2 and 20 kg of paraffin/kg of catalyst/hour; a hydrogen:-paraffin molar ratio in the range of from 0.5:1 to 50:1; and an overall pressure between 1 and 70 bar. Preferred conditions are: a temperature between 220° and 280° C.; a space velocity between 1 and 5 kg of paraffin/kg of catalyst/hour; a hydrogen: paraffin molar ratio in the range of from 1:1 to 15:1; and an overall pressure between 20 and 50 bar. In most cases it is not necessary to use pure hydrogen; hydrogen-containing gases may also be used. A hydrogen-rich gas obtained in the catalytic reforming of hydrocarbon mixtures, such as naphtha, is very suitable.

Finally, the invention relates to a catalyst for the conversion of hydrocarbons in the presence of hydrogen, which catalyst consists partly or entirely of a catalytically active metal silicate prepared by the method described hereinbefore.

The invention is now further elucidated with the aid of the following examples.

EXAMPLE 1

Preparation of catalytically active metal silicate 119.0 g of a silica-alumina containing 21.6%w $Al_2O_3$ and 13.8%w water, calculated on the total weight, was dispersed in 220 g of deionized water. A quantity of 195.3 g of nickel acetate. $4H_2O$ was added with stirring to the resulting slurry which was subsequently evaporated to a volume of 330 ml. After the addition with stirring of 10.38 g of ammonium fluoride, the slurry was heated to 295° C. in a 0.5-liter autoclave in 3 hours and maintained at that temperature for 64 hours. The autoclave was subsequently cooled to room temperature in about 5 hours and the resulting product was filtered, washed and dried at 120° C. The yield was 162 g of dried material. The nickel-substituted synthetic mica-montmorillonite thus prepared has the following composition per unit cell (computed from chemical and X-ray analyses): [octahedral $(Al_{1.08}Ni_{4.38})$] [tetrahedral $(Si_{6.62}Al_{1.38})$] $O_{20}(OH)_{3.24}F_{0.76}(NH_4)_{1.38}$.

3 g of the dried Ni-SMM was suspended in a solution of 53 mg $Pd(NH_3)_4Cl_2$ in 100 ml water and stirred for 16 hours followed by washing of the product with 50 ml water, filtration and drying at 120° C. for 16 hours. The resulting product contained 0.7%w of palladium and was subsequently subjected to "dry" impregnation with a 18.5%w HCl solution. After this the silicate contained 13.0%w of chlorine. Subsequently, it was dried for a half hour at 120° C. and calcined for 1 hour at 540° C. The catalyst thus prepared contains 0.59%w of chlorine.

A comparative catalyst was prepared entirely as described hereinbefore but omitting the impregnation with hydrochloric acid and the subsequent drying. The comparative catalyst contained less than 0.05%w of chlorine.

EXAMPLE 2

Hydroisomerization of Pentane

Pentane hydroisomerization experiments were carried out in a microflow tubular reactor with a length of 35 cm and an inner diameter of 1 cm, containing 2 g of catalyst particles (sieve fraction 0.18–0.59 mm).

Before being used in the catalytic conversion of hydrocarbons in the isomerization reactor, the catalysts of Example 1 were hydrotreated at a pressure of 1 bar and a temperature of 343° C. for 16 hours.

After the catalyst had been subjected to the activating treatment with hydrogen at 343° C. in the tubular reactor, the temperature of the latter was lowered to 250° C. and subsequently a pre-dried normal pentane feed together with pure hydrogen, was passed over the catalyst.

The reaction conditions in the hydroisomerization are:

temperature: 250° C.
total pressure: 30 bar
hydrogen/n-pentane molar ratio: 1.25
space velocity: 2 g pentane/g catalyst/hour The product stream was continuously analysed by means of gas-liquid chromatography. The results, in percentages by weight, are summed up in the following Table.

TABLE

| Catalyst prepared | $nC_5$ conversion | Selectivity to $iC_5$ | Selectivity to cracking | $\dfrac{iC_5}{iC_5 + nC_5} \times 100$ |
|---|---|---|---|---|
| with $HCl/H_2O$ | 67 | 97 | 3 | 66 |
| without $HCl/H_2O$ | 60 | 97 | 3 | 59 |

These examples illustrate that the hydroisomerization catalyst which has been treated with hydrochloric acid according to the invention provides a higher degree of conversion without changing the selectivity, which results in a larger percentage by weight of isopentane on the total quantity of pentanes.

What is claimed is:

1. A process for the hydroisomerization of paraffin hydrocarbons in the presence of hydrogen under suitable reaction conditions, wherein the catalyst used therein is a catalytically active metal silicate comprising an at least partly crystalline metal silicate having a crystal lattice which consists substantially of a triplex layer structure containing in the central layer octahedrally coordinated aluminum which may be entirely or partly substituted by one or more metals from Group VIII of the Periodic Table of Elements, and in the two outer layers tetrahedrally coordinated silicon which may be entirely or partly substituted by aluminum, and wherein said metal silicate is treated by contact with one or more compounds comprising chlorine which can further release one or more protons and/or hydrogen chloride.

2. The process of claim 1 wherein the metal silicate consists at least partly of synthetic mica-montmorillonite in which nickel is the metal substituted for the aluminum.

3. The process of claim 2 wherein the catalytically active metal silicate contains from 20 to 35%w nickel.

4. The process of claim 3 wherein the active halogen is hydrochloric acid and 15–25%w of the hydrochloric acid consists of hydrogen chloride and wherein the metal silicate is calcined after the hydrochloric acid treatment.

5. The process of claim 4 wherein after calcination the catalytically active metal silicate contains from 0.2 to 2%w chlorine and the metal silicate is loaded with one or more noble metals from Group VIII of the Periodic Table of Elements and/or compounds thereof.

6. The process of claim 2 wherein before the conversion is started the catalyst is activated by means of a hydrotreatment carried out at a temperature of from 150° C. to 600° C. and preferably of from 300° C. to 450° C.

7. The process of claim 6 wherein the metal silicate is cross-linked by mixing with aluminum hydrochloride and subsequently heating to at most 600° C. and wherein the metal silicate is loaded with 0.05–5%w or palladium, calculated on total quantity of catalyst.

8. The process of claim 6 wherein paraffins with 4–7 carbon atoms are catalytically isomerized in the presence of hydrogen at a temperature between 150° and 300° C.; a space velocity between 0.2 and 20 kg of paraffins/kg of catalyst/hour; a hydrogen: paraffin molar ratio in the range of from 0.5:1 to 50:1; and an overall pressure between 1 and 70 bar.

* * * * *